United States Patent [19]

Steidl et al.

[11] Patent Number: 5,417,881
[45] Date of Patent: May 23, 1995

[54] STABLE 3,3'-DICHLOROBENZIDINE DIHYDROCHLORIDE SUSPENSION

[75] Inventors: Dieter Steidl, Hofheim am Taunus; Peter Dopfer; Wolfgang Ebertz, both of Frankfurt am Main; Ernst Schutt, Mörfelden, all of Germany

[73] Assignee: Hoechst Aktiengesellschaft, Frankfurt am Main, Germany

[21] Appl. No.: 150,418

[22] Filed: Nov. 10, 1993

[30] Foreign Application Priority Data

Nov. 10, 1992 [DE] Germany .................. 42 37 816.8

[51] Int. Cl.$^6$ ................ B01J 13/00; C09D 11/00; C09K 3/00
[52] U.S. Cl. .................... 252/182.29; 252/182.12
[58] Field of Search ................ 252/182.12, 182.29

[56] References Cited

U.S. PATENT DOCUMENTS

| | | | |
|---|---|---|---|
| 4,341,701 | 7/1982 | Pechey et al. | 8/509 |
| 4,559,160 | 12/1985 | Schultz . | |
| 5,208,376 | 5/1993 | Habig et al. | 564/309 |

FOREIGN PATENT DOCUMENTS 1042456 1/1987 Japan .
9107377 5/1991 WIPO .

*Primary Examiner*—Philip Tucker
*Assistant Examiner*—Joseph D. Anthony

[57] ABSTRACT

By means of a 3,3'-dichlorobenzidine dihydrochloride suspension in hydrochloric acid, comprising the components a) 35 to 63.5% by weight of 3,3'-dichlorobenzidine dihydrochloride;
b) 11 to 24% by weight of hydrogen chloride;
c) and 25 to 55% by weight of-water, in each case relative to the total weight of the suspension (100% by weight) and with the proviso that the components a), b) and c) together make 100% by weight;

and whose viscosity is in the range from 80 to 1400 mPa.s, 3,3'-dichlorobenzidine dihydrochloride can be stably suspended in hydrochloric acid at high concentration and consequently low water content and at the same time a suspension having low viscosity can be obtained, so that the slurry flows out of containers without problems even after relatively long static storage.

14 Claims, No Drawings

STABLE 3,3'-DICHLOROBENZIDINE DIHYDROCHLORIDE SUSPENSION

DESCRIPTION

Stable 3,3'-Dichlorobenzidine Dihydrochloride Suspension

The present invention relates to a 3,3'-dichlorobenzidine dihydrochloride suspension, which is distinguished by a low viscosity and a low settling rate of the solid.

3,3'-Dichlorobenzidine is an industrially relevant starting material for the preparation of azo colorants.

The requirements of occupational hygiene when working with 3,3'-dichlorobenzidine or its dihydrochloride make measures necessary which reduce the contact of man and the environment with this substance to a minimum. To prevent exposure due to dusts of 3,3'-dichlorobenzidine dihydrochloride (DCBDC), processing in suspension is the process of choice. When processing a suspension of the crystallizate of said compound directly from production, technical problems occur due to the rapid sedimentation behavior of a thus produced so-called "mash". Once sedimented, the dihydrochloride can only be suspended again with a high stirring effort. A suspension of this type is unsuitable for transportation to further users.

According to U.S. Pat. No. 4,559,160, stable suspensions, so-called slurries, of 3,3'-dichlorobenzidine dihydrochloride can be prepared by wet-grinding in dilute mineral acids. As low a settling rate as possible together with as low a viscosity as possible is desired here. The viscosity serves as a measure for the handling-ability with reference to the pumpability and flow behavior from containers. The settling behavior is dependent on the acid concentration and the solids content. Said US patent teaches that the content of DCBDC must be between 35 and 50 percent by weight, preferably about 40 percent by weight, relative to the free diamine, the acid content must be between 1 and 10 percent by weight, preferably between 1 and 5 percent by weight, and the water content must be between 40 and 50 percent by weight in order to meet the demands made. Furthermore, it emerges from Example III of said U.S. patent that the sedimentation of 35 to 45 percent strength by weight DCBDC suspensions tends to increase if the acid concentration is increased stepwise from 3 to 10 percent by weight. For the person skilled in the art, it ensues from these results that an increase in the acid concentration above 10% by weight in suspensions having a content of 35 to 45% by weight of DCBDC has a disadvantageous effect on the desired sedimentation behavior. In the case of suspensions having a content of DCBDC above 50% by weight, the effect of the acid concentration on sedimentation is negligibly small, but such concentrated suspensions are very viscous and difficult to pump.

The object of the present invention was therefore to make available a stable DCBDC suspension which has as high a concentration of DCBDC and hydrochloric acid as possible and therefore as low a volume and as low a water content as possible and at the same time has as low a viscosity as possible.

It was found that the object of the present invention can surprisingly be achieved by a higher hydrochloric acid concentration than described in the prior art.

The present invention relates to a stable 3,3'-dichlorobenzidine dihydrochloride suspension in hydrochloric acid, comprising the components a) 35 to 63.5% by weight, preferably 35 to 55% by weight, of 3,3'-dichlorobenzidine dihydrochloride;

b) 11 to 24% by weight, preferably 14 to 19% by weight, of hydrogen chloride, and c) 25 to 55% by weight, preferably 32 to 45% by weight, of water, in each case relative to the total weight of the suspension (100% by weight) and with the proviso that the components a), b) and c) together make 100% by weight; and whose viscosity is in the range from 80 to 1400, preferably 200 to 800, mPa.s.

The present invention also relates to a process for the preparation of the DCBDC suspension according to the invention, which comprises stirring 3,3'-dichlorobenzidine dihydrochloride with a 17 to 37% strength by weight aqueous hydrochloric acid, preferably with concentrated hydrochloric acid, so that a mash having a solids content of 35 to 63.5% by weight results, and then wet-grinding the mash in a suitable apparatus until the mean grain size ($d_{50}$) of the DCBDC particles is between 10 and 40 μm, preferably 15 and 25 μm.

The DCBDC employed for the preparation of the mash is preferably in crystalline form. "Mash" in this connection is understood as meaning an unground, aqueous DCBDC suspension in which the solid still settles relatively rapidly. In order to prevent sedimentation as far as possible, the mash is wet-ground in a suitable apparatus, preferably in a colloid mill which operates on the rotor-stator principle, or in a mill which utilizes grinding media as grinding materials, for example ball mills or stirred ball mills, until the grain size of the DCBDC particles in the resulting suspension is in the above-mentioned range.

During grinding to mean grain sizes of below 10 μm, the viscosity of the suspension greatly increases, and thixotropic behavior is additionally observed. Such finely ground suspensions are not suitable for the application area according to the invention.

A measure of the sedimentation of a solid in a suspension is the so-called settling rate, defined as the quotient of settled volume and total volume. To determine this quotient, a specific volume of a suspension (total volume) is poured into a measuring cylinder and the suspension is allowed to sediment for a specific given time, for example 24 hours. After this time, the volume which is still in the suspended state is measured, A suspension in which the particles are completely suspended has a settling rate of 1.0. For the purpose according to the invention, settling rates of 0.9 and above, after a standing time of 72 hours, are suitable. After 24 hours, for example, the settling rates of the solid in the case of a 50% strength by weight suspension are in the range between 0.95 and 0.99 and in the case of a 35% strength by weight suspension in the range between 0.92 and 0.98 and, after 72 hours, in the range between 0.90 and 0.94.

The suspension according to the invention also runs from containers without problems after relatively long, static storage. Even in winter temperatures down to −10° C., the suspension according to the invention tends neither to freeze nor to thicken. Contamination-free handling for the user is thus possible. Owing to the relatively low water content of the suspension according to the invention in comparison to the DCBDC suspensions known in the prior art, the transportation costs can be reduced, the space-time yield in the synthesis of the corresponding azo colorant increased and the amounts of effluent decreased.

The azo pigments prepared from 3,3'-dichlorobenzidine or its hydrochloride are of relatively great importance in the range of azo colorants, in particular in half-tone gravure printing and offset printing.

In the following examples, which are only used for illustration and are not to be regarded as a restriction of the present invention, percentages are in each case percentages by weight.

EXAMPLES

Hydrochloric acid and optionally water are introduced into a weighed stirring container in the desired ratio. 3,3'-Dichlorobenzidine dihydrochloride in the required amount is added with stirring via a filling device. The mash prepared in this way is fed to a stirred ball mill by means of a controlled rotational speed peristaltic pump. After a single passage through the mill, the ground suspension is collected in a storage vessel.

In Table 1 which follows, the batch size is in each case 14 kg of suspension. The percentage data are percentages by weight, relative to the total weight of the suspension. The residence times are average values and are calculated from the throughput and free volume of the ball mill.

TABLE 1

| Example | % HCl | % H$_2$O | % DCBDC | Residence time in min |
| --- | --- | --- | --- | --- |
| 1 | 15 | 35 | 50 | 5.2 |
| 2 | 15 | 35 | 50 | 3.5 |
| 3 | 15 | 42 | 40 | 5.6 |
| 4 | 14.5 | 31.5 | 54 | 5.6 |
| 5 | 15 | 35 | 50 | 2.4 |
| 6 | 11.7 | 38.3 | 50 | 5.5 |
| 7 | 16.4 | 33.6 | 50 | 5.4 |
| 8 | 18.6 | 31.4 | 50 | 5.5 |

In Table 2 which follows, the viscosity, the settling rate after a standing time of 24 hours and the mean grain size (d$_{50}$) of the DCBDC particles are compared as the result of the experiments.

TABLE 2

| Example | Viscosity in mPas | Settling rate in ml/ml | d$_{50}$ in μm |
| --- | --- | --- | --- |
| 1 | 580 | 0.982 | 17 |
| 2 | 215 | 0.976 | 28 |
| 3 | 210 | 0.977 | 22 |
| 4 | 470 | 0.990 | 18 |
| 5 | 82 | 0.954 | 36 |
| 6 | 395 | 0.988 | 22 |
| 7 | 570 | 0.984 | 18 |
| 8 | 630 | 0.992 | 26 |

We claim:

1. A stable 3,3'-dichlorobenzidine dihydrochloride suspension comprising:
   a) 35 to 63.5% by weight of suspended solid particles of 3,3'-dichlorobenzidine dihydrochloride,
   b) 11 to 24% by weight of hydrogen chloride, and
   c) and 25 to 55% by weight of water, in each case the said weight percents being relative to the total weight of the suspension (100% by weight) and with the proviso that the components a), b) and c) together make 100% by weight;
   wherein the viscosity of said suspension is in the range from 80 to 800 mPa.s.

2. A suspension as claimed in claim 1, wherein the suspension contains 35 to 55% by weight of 3,3'-dichlorobenzidine dihydrochloride, relative to the total weight of the suspension.

3. A suspension as claimed in claim 1, wherein the suspension contains 14 to 19% by weight of hydrogen chloride, relative to the total weight of the suspension.

4. A suspension as claimed in claim 1, wherein the suspension contains 35 to 45% by weight of water, relative to the total weight of the suspension.

5. A suspension as claimed in claim 1, wherein the viscosity of the suspension is in the range from 200 to 800 mPa.s.

6. A suspension as claimed in claim 1, wherein the mean grain size of the solid particles is between 10 and 40 μm.

7. A suspension as claimed in claim 1, wherein the mean grain size of the solid particles is between 15 and 25 μm.

8. A stable 3,3'-dichlorobenzidine dihydrochloride suspension comprising:
   a) 35 to 55% by weight of suspended solid particles of 3,3'-dichlorobenzidine dihydrochloride,
   b) 14 to 19% by weight of hydrogen chloride, and
   c) 32 to 45% by weight of water,
   in each case the said weight percents being relative to the total weight of the suspension (100% by weight) and with the proviso that the components a), b) and c) together make 100% by weight;
   wherein the viscosity of said suspension is in the range from 200 to 800 mPa.s.

9. A suspension as claimed in claim 8, wherein the mean grain size of the solid particles is between 10 and 40 μm.

10. A suspension as claimed in claim 8, wherein the mean grain size of the solid particles is between 15 and 25 μm.

11. A process for the preparation of a stable 3,3'-dichlorobenzidine dihydrochloride suspension, which comprises stirring 3,3'-dichlorobenzidine dihydrochloride with a 17 to 37% strength by weight aqueous hydrochloric acid, so that a mash having a solids content of 35 to 63.5% by weight results, and then wet-grinding the mash in a suitable apparatus until the man grain size (d$_{50}$) of the 3,3'-dichlorobenzidine dihydrochloride particles is between 10 and 40 μm; the resulting stable 3,3'-dichlorobenzidine dihydrochloride suspension containing 35 to 63.5% by weight of 3,3'-dichlorobenzidine dihydrochloride, 11 to 24% by weight of hydrogen chloride and 25 to 55% by weight of water wherein the viscosity of said suspension is in the range from 200 to 800 mPa. s.

12. The process as claimed in claim 11, wherein the mash is ground in a colloid mill which operates on the rotor-stator principle, or in a ball mill or stirred ball mill.

13. The process as claimed in claim 11, wherein the resulting stable 3,3'-dichlorobenzidine dihydrochloride suspension contains 35 to 55% by weight of 3,3'-dichlorobenzidine dihydrochloride, 14 to 19% by weight of hydrogen chloride and 32 to 45% by weight of water.

14. The process as claimed in claim 13, wherein the mash is ground in a colloid mill which operates on the rotor-stator principle, or in a ball mill or stirred ball mill.

* * * * *